United States Patent
Meegan (10) Patent No.: US 10,196,479 B2
(45) Date of Patent: *Feb. 5, 2019

(54) MODIFIED AMINE CURING AGENTS, THEIR PREPARATION AND USE IN CURABLE COMPOSITIONS

(71) Applicant: CYTEC INDUSTRIES INC., Princeton, NJ (US)

(72) Inventor: Jonathan E. Meegan, Chester (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/990,058

(22) Filed: May 25, 2018

(65) Prior Publication Data

US 2018/0273677 A1  Sep. 27, 2018

Related U.S. Application Data (63) Continuation of application No. 14/953,738, filed on Nov. 30, 2015, now Pat. No. 10,011,679.

(30) Foreign Application Priority Data

Dec. 2, 2014  (GB) .................................. 1421373.0

(51) Int. Cl.
*C07C 211/50*  (2006.01)
*C08G 59/50*  (2006.01)
(Continued)

(52) U.S. Cl.
CPC ........ *C08G 59/5033* (2013.01); *C07C 211/50* (2013.01); *C08J 5/24* (2013.01); *C08K 5/18* (2013.01); *C08J 2363/00* (2013.01)

(58) Field of Classification Search
CPC ............... C08G 59/5033; C07C 211/50; C08L 63/00–63/10; C09D 163/00–163/10;
(Continued)

(56) References Cited

U.S. PATENT DOCUMENTS 3,563,906 A  2/1971  Hoeschele
4,900,848 A  2/1990  Saito et al.
(Continued)

FOREIGN PATENT DOCUMENTS

EP  0203828 B1  3/1990
EP  0591313 B1  4/1997
(Continued)

OTHER PUBLICATIONS

International Search Report. PCT/US2015/062901. dated Jan. 19, 2016.

*Primary Examiner* — Kregg T Brooks
(74) *Attorney, Agent, or Firm* — Thi Dang (57) ABSTRACT

A method for producing a modified form of an aromatic amine compound represented by the following structure I:

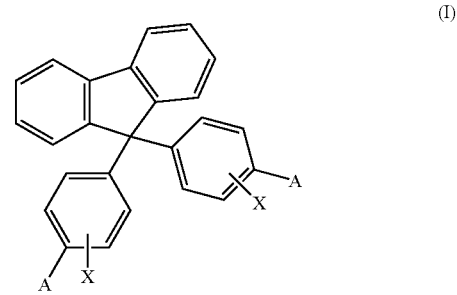

where A is an amine group —NHR, R is independently selected from hydrogen, linear and branched alkyl groups having 1 to 6 carbon atoms, preferably A is $NH_2$; X is a halogen selected from Cl, Br, F, I, and At,
(Continued)

or hydrogen (H). The method includes heating the aromatic amine compound, in its initial crystalline form, to a temperature above its melting point in order to obtain a molten material, then cooling the molten material to a temperature below the melting point of the crystalline compound so as to produce an amorphous, glassy form of the aromatic amine compound. The modified aromatic amine compound is suitable as a curing agent in resin compositions that are used for fabricating fiber-reinforced composites.

6 Claims, 5 Drawing Sheets

(51) Int. Cl.
  *C08J 5/24* (2006.01)
  *C08J 5/04* (2006.01)
  *C08K 5/18* (2006.01)
  *C08L 63/00* (2006.01)

(58) Field of Classification Search
  CPC .............................. C09J 163/00–163/10; C08J 2363/00–2363/10; C08K 5/18
  See application file for complete search history.

(56) References Cited

U.S. PATENT DOCUMENTS

| | | |
|---|---|---|
| 5,073,595 A | 12/1991 | Almer et al. |
| 5,369,192 A | 11/1994 | Ko et al. |
| 5,461,090 A | 10/1995 | Sweet |
| 5,541,000 A | 7/1996 | Hardy et al. |
| 5,648,407 A | 7/1997 | Goetz et al. |
| 6,577,492 B2 | 6/2003 | O'Bryan, Jr. |
| 7,141,303 B2 | 11/2006 | Clemens et al. |
| 7,709,582 B2 | 5/2010 | Kouchi et al. |
| 2004/0110958 A1 | 6/2004 | Nishiyama et al. |
| 2008/0194878 A1 | 8/2008 | Nishiyama et al. |
| 2010/0222461 A1 | 9/2010 | Bongiovanni et al. |
| 2011/0049426 A1 | 3/2011 | Patel et al. |
| 2011/0143138 A1 | 6/2011 | Eggers et al. |
| 2013/0090414 A1 | 4/2013 | Mortimer |
| 2013/0225788 A1 | 8/2013 | Meegan |
| 2014/0228519 A1 | 8/2014 | Nakayama et al. |

FOREIGN PATENT DOCUMENTS

| | | |
|---|---|---|
| EP | 2441746 A1 | 4/2012 |
| EP | 2426157 A1 | 7/2012 |
| EP | 1817376 B1 | 8/2012 |
| GB | 2506476 A | 4/2014 |
| WO | 9711112 A1 | 3/1997 |
| WO | 9808906 A1 | 3/1998 |

FIG. 1

Bulk material

FIG.2

Ground bulk material

MODIFIED AMINE CURING AGENTS, THEIR PREPARATION AND USE IN CURABLE COMPOSITIONS

This application is a Continuation Application of U.S. application Ser. No. 14/953,738 filed on Nov. 30, 2015, which claims the benefit of United Kingdom Application No. 1421373.0 filed on Dec. 2, 2014, both of which are incorporated by reference in theft entirety.

Fiber-reinforced composite materials that consist of reinforcement fibers embedded in a matrix resin have been used in sporting goods as well as high-performance structures such as parts of airplanes and automobiles due mainly to the fact that they are lightweight but high in strength. Thermoset resin, particularly epoxy resins, have been widely used as matrix resins for such fiber-reinforced composites because of their desirable characteristics such as thermal and chemical resistance, adhesion and abrasion resistance. Epoxy resins are monomers or precursors that react with curing agents to yield high-performance resins. Curing agents that are widely used with epoxy resins for producing fiber-reinforced composite materials to be used in the aircraft manufacturing include, among others, aromatic polyamines. The structure of the curing agents and the reactivity of their functional groups are often used to control the reaction rate and the process-ability of the resin compositions.

DETAILED DESCRIPTION

While properties such as viscosity and glass transition temperature (TO of epoxy-based compositions may depend on the choice of the curing agent, these properties cannot be conveniently be adjusted with the available curing agents. Many aromatic polyamine curing agents are crystalline materials with a high melting point which makes the processing conditions for preparing resin compositions and forming composite materials therefrom very restricted. More specifically, the epoxy resin composition containing high-melting curing agent is normally required to be heated at a high temperature exceeding 120° C. so as to obtain a homogeneous blend of the epoxy resin and polyamine curing agent. Such high-temperature treatment causes rapid hardening reaction of the epoxy resin composition. As a result, the temperature range for which the epoxy resin composition can be used for forming fiber-reinforced composite materials, such as partially-cured prepregs, or for infusing a fibrous preform via RTM, is narrow and the process tolerance is small.

As an example, 9,9-Bis(4-amino-3-chlorophenyl)fluorene (or CAF), has been conventionally used as a curing agent in epoxy-based formulations. CAF is normally a crystalline solid with a high melting point of about 205° C. To form a homogenous mixture with the epoxy resins, the CAF material is usually dissolved into the epoxy resin at a temperature range of 140° C. to 160° C. Such high temperatures can severely limit the applications to which the epoxy formulations can be applied due to concerns over the likelihood of a self-accelerating decomposition event occurring in the resin.

Another issue for processing using epoxy-based formulations is relating to the safe pot-life time period of resin formulations for Resin Transfer Molding (RTM) during processing. In conventional RTM processes, the liquid resin is injected under pressure into a fibrous preform placed in a closed mold, or a fibrous preform placed in a one-sided open mold and then covered with a vacuum bag, followed by vacuuming for resin injection, the latter process being called Vacuum Assisted Resin Transfer Molding (VaRTM).

When the epoxy-based resin formulation containing amine curing agent therein is stored in a container (particularly a heated container), the safe-storage time decreases as the storage temperature increases due to chemical reaction between the resin and the cure agent, as the storage temperature increases the kinetics, and heat generation of these reactions also increases: above a temperature threshold this increase is independent of that expected from the storage temperature and detrimental to the safety of the process. Such a trend is problematic in production processes as it determines the maximum amount of time, or storage temperature that resin can have at specific points in the process cycle; this in turn limits the quantity and throughput of a process utilising the resin. If the interaction of the epoxy and amine functionalities could be reduced until the point in the production process that requires the fully formulated resin system, then safety factor associated with storing the resin could be increased dramatically. One method that is regularly used in for RTM is to provide a two-part resin system, where the epoxy component and the cure agent are stored in separate tanks until the point at which they are required to be mixed together. However, in applying this technique to resin formulations for RTM, a unique problem occurs in that some curing agents possess a high melting temperature which is outside the range over which a standard two-part RTM equipment is capable of operating.

A method for the modification of certain amine curing agents is disclosed to obtain an amorphous, glassy form which does not suffer the problems associated with the higher melting curing agents discussed above. The modification can be applied to the following aromatic amine compounds represented by structure I:

(I)

where A is a primary or secondary amine group (A=—NHR, where R is independently selected from hydrogen, linear and branched alkyl groups having 1 to 6 carbon atoms), in some embodiments, A is $NH_2$; X is a halogen selected from Cl, Br, F, I, and At, or hydrogen (H);

In one embodiment, the amine compound of structure I is 9,9-Bis(4-amino-3-chlorophenyl)fluorene (or CAF), represented by the following structure:

In another embodiment, the amine compound of structure I is 9,9-Bis(4-aminophenyl)fluorene, represented by the following structure:

The above aromatic amine compounds are normally in the form of crystalline solids at room temperature. It has been discovered that the amorphous, glassy form of these amine compounds does not suffer the problems associated with the higher melting point of their original crystalline form.

The term "amorphous" refers to a non-crystalline solid that lacks the long-range order characteristic of a crystal. A crystalline solid has a sharp melting point, i.e., it changes into the liquid state at a definite temperature, which is easily identified using a technique such as Differential Scanning calorimetry (DSC). On the contrary, an amorphous solid does not have a sharp melting point. Rather, the amorphous solid has a softening or glass transition temperature at which it softens upon heating and starts to flow without undergoing any abrupt or sharp change from solid to liquid phase. The amorphous, glassy state of the amine compounds disclosed herein can be verified by DSC and the presence of a glass transition, without evidence of melting above the glass transition temperature, and the level of crystallinity in a structure can also be qualitatively estimated by Cross Polarised Optical Microscopy.

As the result of modification, the amorphous, glassy form of the individual aromatic amines or mixture thereof, has a lower melting point (or softening temperature) and can be dissolved into epoxy resins at lower temperatures, e.g. less than 140° C., to form substantially homogeneous mixtures. The advantage of such lower dissolution temperatures is that the amorphous, glassy form can conveniently be used at lower temperatures to provide a homogeneous mixture with the resin component. This overcomes the need of heating the mixture of epoxy resin and curing agent above the melting point of the crystalline curing agent.

Another benefit of the amorphous form of the curing agents is that the amorphous substance remains stable indefinitely due to the fact that it possesses no detectible recrystallization energy as determined by DSC. As such, the amorphous, glassy substance is particularly suitable for a two-part RTM formulation, where the epoxy resin component is stored and contained separately from the curing agent component until the time of usage.

Another aspect of the present disclosure is pertaining to a curable epoxy-based composition that is suitable for the fabrication of high-strength composite materials via conventional prepregging technique or liquid resin infusion, e.g. RTM. The curable epoxy-based composition may contain:

(a) an epoxy component, which includes at least one polyepoxide, and (b) an amorphous, glassy form of an aromatic amine compound represented by either structure I or II disclosed above, or an amorphous, glassy mixture of the two or more aromatic amine compounds.

The stoichiometry for components (a) and (b) is such that the amine component (b) is present in an amount sufficient to provide 0.5 to 1.1 amino groups per epoxy group present in the epoxy component. The term "polyepoxide" refers a compound that contains more than one epoxide group:

When the fluorenyl amine compound of structure I or II is used in the epoxy composition, certain benefits can be achieved. That is, upon curing, the cured resin exhibits a high glass transition temperature ($T_g$) and a low degree of moisture pick-up, and furthermore, the cured resin does not exhibit a substantial reduction in $T_g$ upon absorption of moisture.

Amorphous Modification Method

The amorphous modification method includes heating the aromatic amine of structure I or II above, in its crystalline form, to a temperature above its melting temperature, as determined by DSC experiment, more specifically, 1° C. to 50° C. above its melting temperature, preferably, 1° C. to 20° C. above, particularly, 2° C. to 15° C. above. The molten substance thus obtained is then cooled to a temperature below the melting point of the original crystalline substance, preferably to about 30° C. or lower, for example, to about 25° C. Cooling does not require any specific apparatus, and the cooling rates of about 1° C./min to about 20° C./min will give excellent results but it is sufficient to let the molten material stand and allow it to reach ambient temperature.

To form an amorphous, glassy mixture of two or more amine compounds, the individual aromatic amines, in crystalline form, are mixed in a proper weight ratio and the mixture is then heated to above the melting point of the individual compounds to obtain a molten mixture. The mixture may be stirred to obtain a homogeneous molten mixture. The molten mixture thus obtained is then cooled to below the melting point of the individual substances, preferably to 30° C. or lower, for example, to 25° C., as described previously. Alternatively, the crystalline compounds can be melted individually and the molten compounds can then be combined to form a molten mixture followed by cooling.

In one embodiment, 9,9-Bis(4-amino-3-chlorophenyl)fluorene (CAF) is heated to beyond its melting point (about 205° C.) and then the molten substance is cooled to ambient temperature (20° C.-25° C.) resulting in the formation of an amorphous glassy material with a melting temperature (or softening temperature) of 85° C. to 90° C. The amorphous material with lower melting temperature is chemically identical to the original crystalline material with a melting point of 205° C. but can be processed at a much lower temperature. As such, the amorphous form of CAF is particularly suitable for a two-part RTM formulation, where the epoxy resin component is contained separately from the curing agent component.

Epoxy-Based Composition

The epoxy component (a) of the curable epoxy-based composition disclosed herein contains one or more epoxy resins, at least one of which is a polyepoxide. Suitable epoxy resins include polyglycidyl derivatives of aromatic diamine, aromatic mono primary amines, aminophenols, polyhydric phenols, polyhydric alcohols, polycarboxylic acids. Examples of suitable epoxy resins include polyglycidyl ethers of the bisphenols such as bisphenol A, bisphenol F, bisphenol S and bisphenol K. Also suitable are epoxy resins which are condensation products of formaldehyde and phenol or its substituent derivative, that is, novolac polyglycidyl ether.

Specific examples are tetraglycidyl derivatives of 4,4'-diaminodiphenylmethane (TGDDM), resorcinol diglycidyl ether, triglycidyl-p-aminophenol, triglycidyl-m-aminophenol, bromobisphenol F diglycidyl ether, tetraglycidyl derivatives of diaminodiphenylmethane, trihydroxyphenyl methane triglycidyl ether, polyglycidylether of phenol-formaldehyde novolac, polyglycidylether of o-cresol novolac or tetraglycidyl ether of tetraphenylethane.

Commercially available epoxy resins suitable for use in the epoxy component include N,N,N',N'-tetraglycidyl diamino diphenylmethane (e.g. MY 9663, MY 720, and MY 721 from Huntsman); N,N,N',N'-tetraglycidyl-bis(4-aminophenyl)-1,4-diiso-propylbenzene (e.g. EPON 1071 from Momentive); N,N,N',N'-tetraclycidyl-bis(4-amino-3,5-dimethylphenyl)-1,4-diisopropylbenzene, (e.g. EPON 1072 from Momentive); triglycidyl ethers of p-aminophenol (e.g. MY 0510 from Hunstman); triglycidyl ethers of m-aminophenol (e.g. MY 0610 from Hunstman); diglycidyl ethers of bisphenol A based materials such as 2,2-bis(4,4'-dihydroxy phenyl) propane (e.g. DER 661 from Dow, or EPON 828 from Momentive, and Novolac resins preferably of viscosity 8-20 Pas at 25° C.; glycidyl ethers of phenol Novolac resins (e.g. DEN 431 or DEN 438 from Dow); di-cyclopentadiene-based phenolic novolac (e.g. Tactix® 556 from Huntsman); diglycidyl 1,2-phthalate (e.g. GLY CEL A-100); diglycidyl derivative of dihydroxy diphenyl methane (Bisphenol F) (e.g. PY 306 from Huntsman). Other epoxy resins include cycloaliphatics such as 3',4'-epoxycyclohexyl-3,4-epoxycyclohexane carboxylate (e.g. CY 179 from Huntsman).

The curable poxy-based composition of the present disclosure may also include a minor amount of tougheners selected from, but are not limited to, thermoplastic polymers (e.g. polyether sulfone (PES), polyamide, polyimide), elastomers (e.g. ATBN), core-shell rubber particles, crosslinked thermoplastic particles. The amount of tougheners may be less than 20% by weight, in some embodiments, less than 7% by weight based on the total weight of the composition.

Composite Materials and Methods of Making

The curable epoxy-based resin composition of the present disclosure may be used to form composite materials such as prepregs (such as those used for making aerospace composite structures. The term "prepreg" as used herein refers to a layer of fibrous material (e.g. unidirectional tows or tape, nonwoven mat, or fabric ply) that has been impregnated with a curable matrix resin.

Prepregs may be manufactured by infusing or impregnating continuous fibers or woven fabric with a matrix resin system, creating a pliable and tacky sheet of material. This is often referred to as a prepregging process. The precise specification of the fibers, their orientation and the formulation of the resin matrix can be specified to achieve the optimum performance for the intended use of the prepregs. The volume of fibers per square meter can also be specified according to requirements.

To form a composite part, a plurality of prepregs is laid up on a molding tool in a stacking arrangement to form a "prepreg layup". The layup process may be done manually or by an automated process such as Automated Tape Laying (ATL). The prepreg plies within the layup may be positioned in a selected orientation with respect to one another. For example, prepreg layups may comprise prepreg plies having unidirectional fiber architectures, with the fibers oriented at a selected angle θ, e.g. 0°, 45°, or 90°, with respect to the largest dimension of the layup, such as the length. Once in place, the prepregs in the layup are consolidated and cured under pressure to achieve the required fiber volume fraction with a minimum of voids.

The term "impregnate" refers to the introduction of a curable resin composition to reinforcement fibers so as to partially or fully encapsulate the fibers with the resin. The impregnating method may include:

(1) Continuously moving fibers through a (heated) bath of molten resin composition to fully or substantially fully wet out the fibers; or (2) Pressing top and bottom resin films against a web of continuous, unidirectional fibers or a continuous fabric ply, while applying heat.

The curable epoxy-based resin composition of the present disclosure may also be formulated for liquid resin infusion, including RTM and VaRTM. For resin infusion, the viscosity of the resin composition may be less than 5 Poise at a temperature in the range of about 80° C. to about 130° C.

A two-part RTM resin system can be provided such that the epoxy resin component and the amine curing agent are kept separately for the maximum amount of time allowed by the process before the components are combined prior to injection into the mold or onto the tool used in the RTM process. The separation of resin and curing agent is advantageous as it minimizes the amount of viscosity development experienced by the formulation as a consequence of reaction between the resin and the curing agent, as a function of time and temperature, if the two components were combined. The result is a resin formulation with improved processing capability and storage stability.

The two-part RTM processing is enabled by the softening of the amine curing agent above its glass transition temperature and the decreasing viscosity as the temperature is increased towards the melting temperature of the crystalline substance. The increase in liquid-like behavior of the amorphous, glassy form of the amine curing agent facilitates pumping and accurate metering of the components so as to maintain the necessary stoichiometry for the epoxy resin and amine curing agent.

Furthermore, the amorphous, glassy form of amine curing agent functions as a lower-temperature solubilizing replacement for the currently used crystalline form. This will allow resin processing at lower temperatures and improve the stability and safety of the current one-component RTM resin formulation.

The reinforcement fibers for fabricating composite materials may take the form of chopped fibers, continuous fibers, filaments, tows, bundles, sheets, plies, and combinations thereof. Continuous fibers may further adopt any of unidirectional (aligned in one direction), multi-directional (aligned in different directions), non-woven, woven, knitted, stitched, wound, and braided configurations, as well as swirl mat, felt mat, and chopped mat structures. Woven fiber structures may comprise a plurality of woven tows, each tow composed of a plurality of filaments, e.g. thousands of filaments. In further embodiments, the tows may be held in position by cross-tow stitches, weft-insertion knitting stitches, or a small amount of resin binder, such as a thermoplastic resin.

The fiber composition includes, but are not limited to, glass (including Electrical or E-glass), carbon, graphite, aramid, polyamide, high-modulus polyethylene (PE), polyester, poly-p-phenylene-benzoxazole (PBO), boron, quartz, basalt, ceramic, and combinations thereof. For the fabrication of high-strength composite materials, e.g. for aerospace and automotive applications, it is preferred that the reinforcing fibers have tensile strength of greater than 3500 MPa.

EXAMPLES

Example 1

Figure 1:
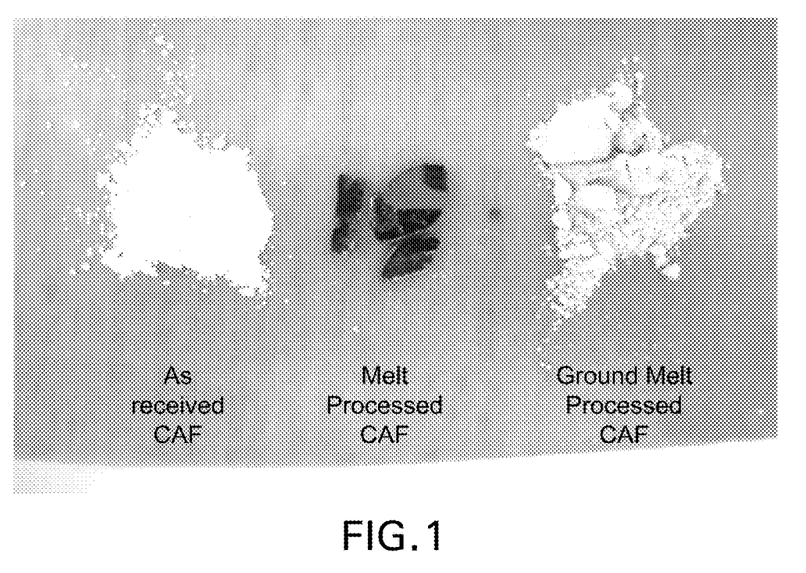
FIG. 1 shows an image of original crystalline 9,9-Bis(4-amino-3-chlorophenyl)fluorene (CAF) CAF prior to heat treatment (left) as compared to the melt material after heating and cooling (center) and the ground melt material after grinding (right).
Figure 2:
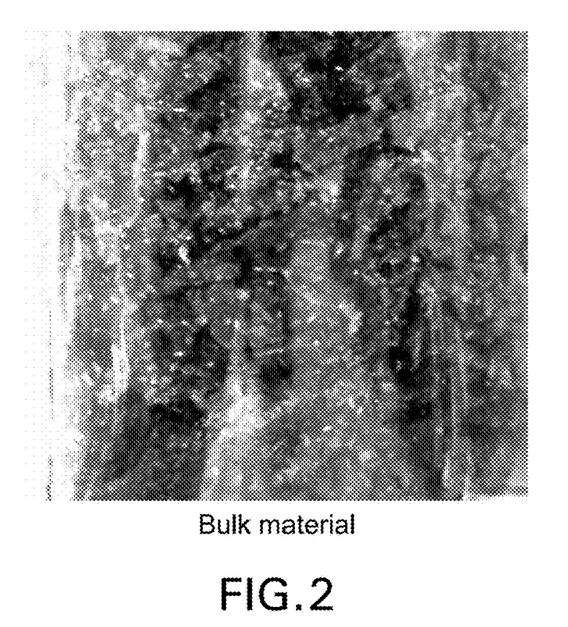
FIG. 2 shows a close-up view of the amorphous, glassy form of CAF as bulk material.
Figure 3:
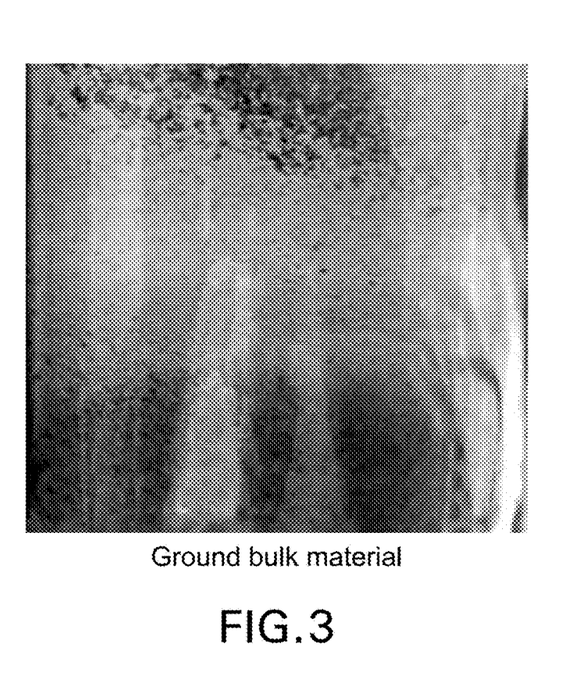
FIG. 3 shows the same amorphous, glassy CAF material of FIG. 2 after grinding.
Figure 4A:
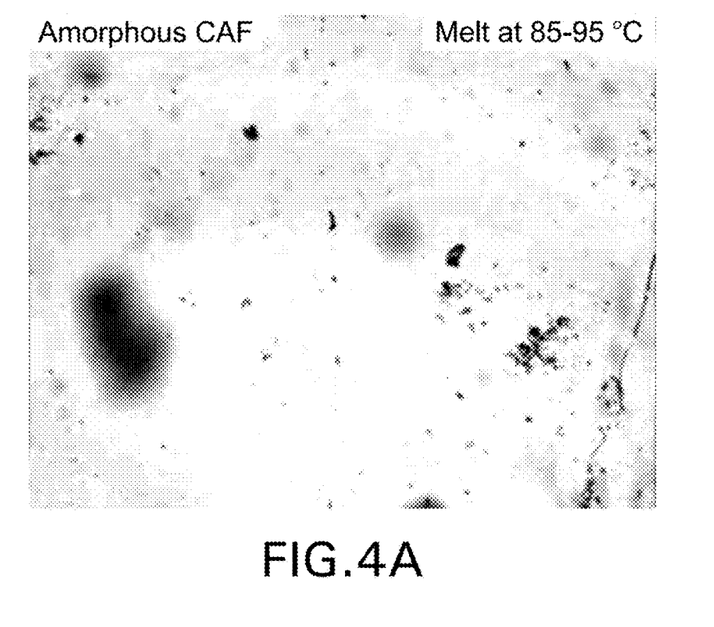
FIG. 4A shows an image of the amorphous CAF as a molten material at 85° C.-95° C.
Figure 4B:
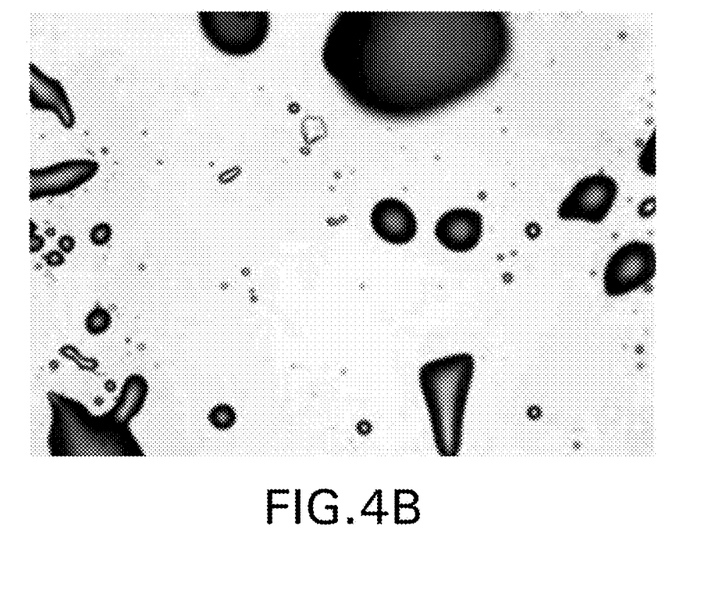
FIG. 4B is a close-up view of the molten material shown in FIG. 4A.
Figure 5:
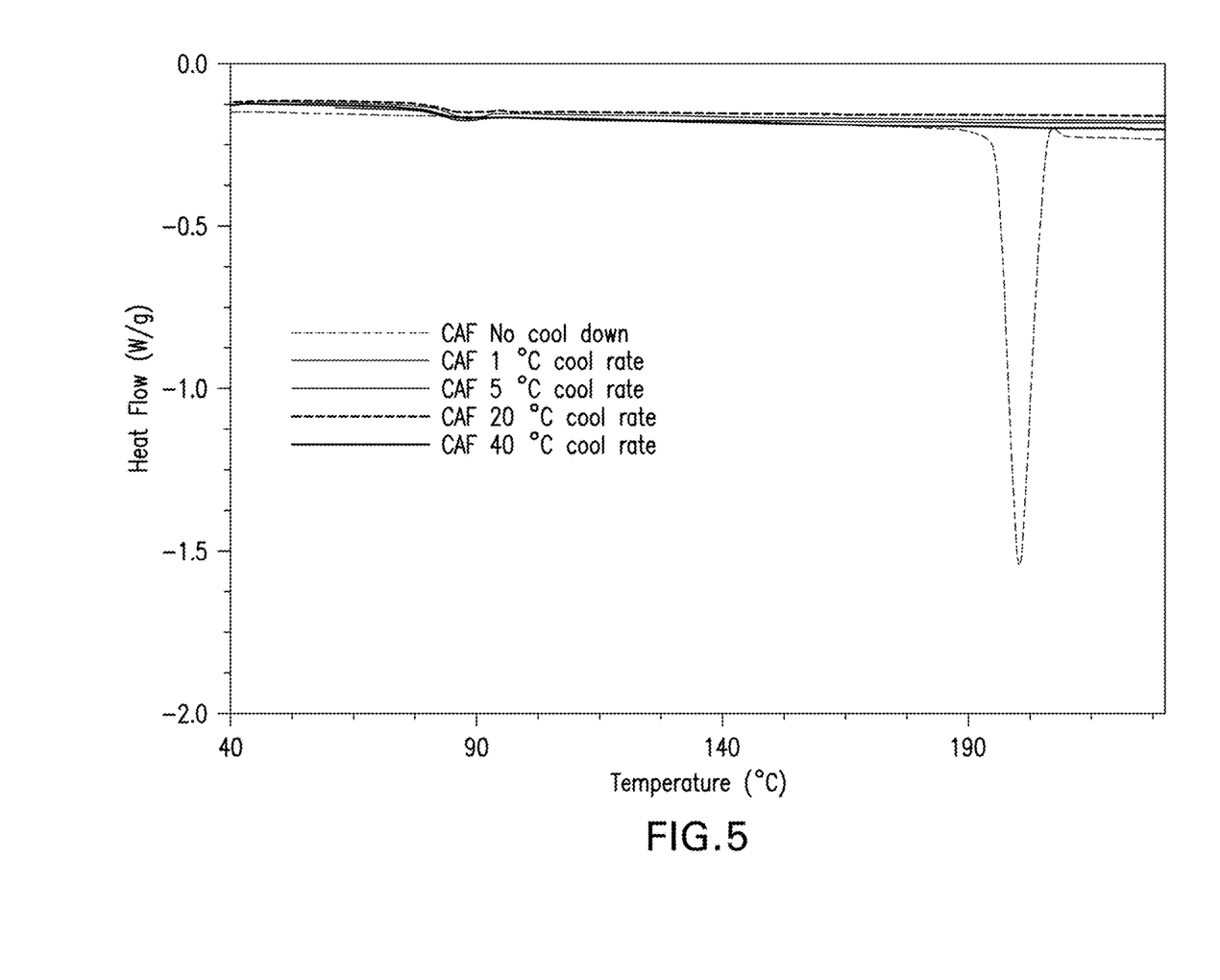
FIG. 5 shows DSC traces for a CAF material demonstrating the effect of cooling rate.
Figure 6:
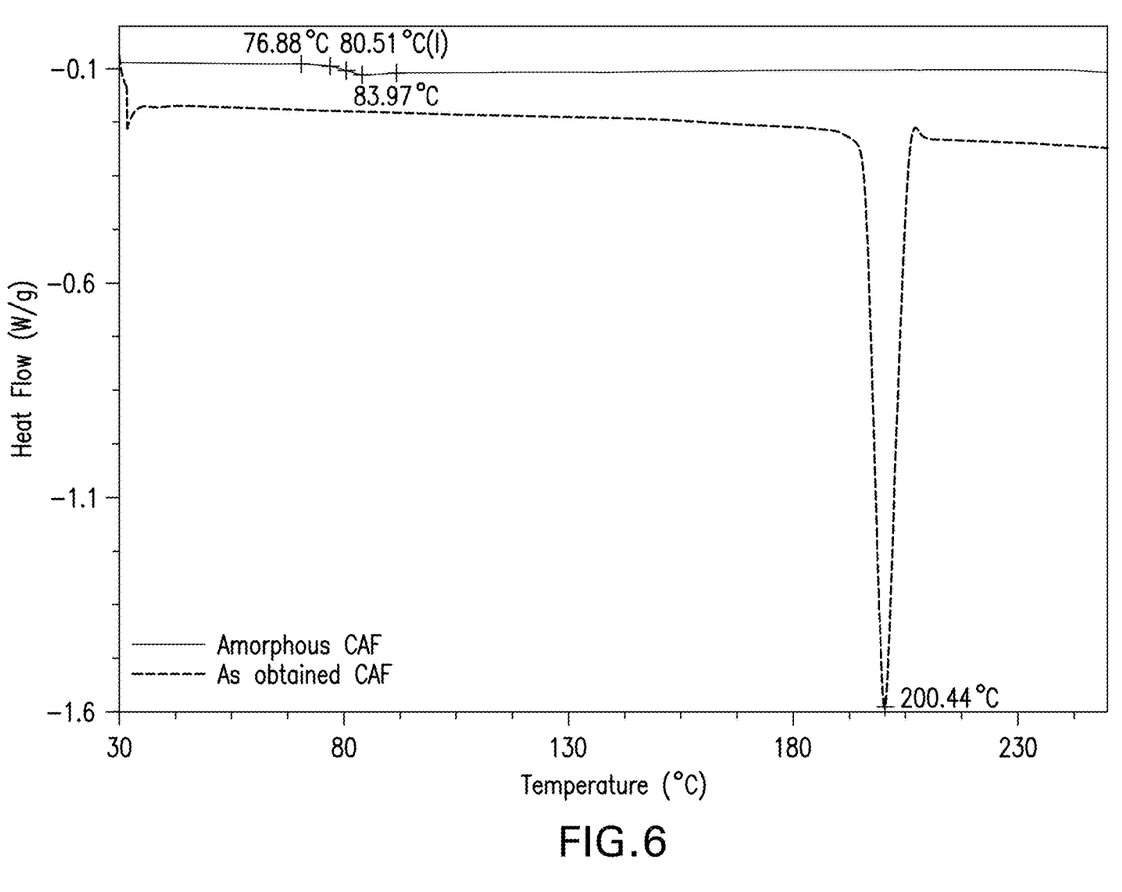
FIG. 6 shows a comparison of amorphous, glassy CAF prepared in an example with the as-received crystalline form of CAF.

10 g of CAF in the form of ground solids was heated in a fan oven to 215° C. and held for 15 minutes followed by cooling to ambient temperature to yield a glassy material with a $T_g$ of 85° C.-95° C. The amorphous, glassy state of the CAF material was proven by DSC analysis performed on a TA Instruments Q2000 DSC FIG. 1 shows an image of the original crystalline CAF prior to heat treatment (left) adjacent to the melt material after heating and cooling (center) and the ground melt material after grinding (right). FIG. 2 shows a close-up view of the amorphous, glassy form of CAF as bulk material, and FIG. 3 shows the same amorphous, glassy material after grinding with a Pestle and Mortar, resulting in a purple powder. FIG. 4A shows an image of the amorphous CAF as a molten material at 85° C.-95° C. FIG. 4B is a close-up view of the same molten material shown in FIG. 4A. FIG. 5 shows DSC traces demonstrating the effect of cooling rate from the melt state on the as-recovered CAF material. FIG. 6 shows a comparison of amorphous, glassy CAF prepared in the example above with the as-received crystalline form of CAF.

DSC analysis of the untreated CAF material confirmed a single melt transition between 195° C. and 205° C. Subsequent quenching experiments from the melt state showed that the obtained material was a glassy amorphous material in the case of each ramp rate with a $T_g$ centered on 80.5° C.

What is claimed is:

1. A curable epoxy-based composition comprising:
   (a) an epoxy component, which includes at least one polyepoxide; and
   (b) an aromatic amine compound in an amorphous, glassy form, represented by the following structure:

2. The curable epoxy-based composition of claim 1, wherein the composition has a viscosity of less than 5 Poise at a temperature in the range of about 80° C. to about 130° C.

3. The curable epoxy-based composition of claim 1, wherein the aromatic amine compound in an amorphous, glassy form is prepared by heating the aromatic amine compound, in its initial crystalline form, to a temperature of 1° C. to 50° C. above its melting point, as determined by Differential Scanning calorimetry (DSC), in order to obtain a molten material, then cooling the molten material to a temperature of 30° C. or lower.

4. A curable epoxy-based composition comprising:
   (a) an epoxy component, which includes at least one polyepoxide; and
   (b) a modified aromatic amine compound in amorphous, glassy form,
   wherein the modified aromatic amine compound is 9,9-Bis(4-amino-3-chlorophenyl) fluorene represented by the following structure:

and
the modified aromatic amine is the only amine compound in amorphous, glassy form.

5. The curable epoxy-based composition of claim 4, wherein the composition has a viscosity of less than 5 Poise at a temperature in the range of about 80° C. to about 130° C.

6. The curable epoxy-based composition of claim 4, wherein the modified aromatic amine compound is prepared by heating the aromatic amine compound, in its initial crystalline form, to a temperature of 1° C. to 50° C. above its melting point, as determined by Differential Scanning calorimetry (DSC), in order to obtain a molten material, then cooling the molten material to a temperature of 30° C. or lower.

* * * * *